Figure 1:
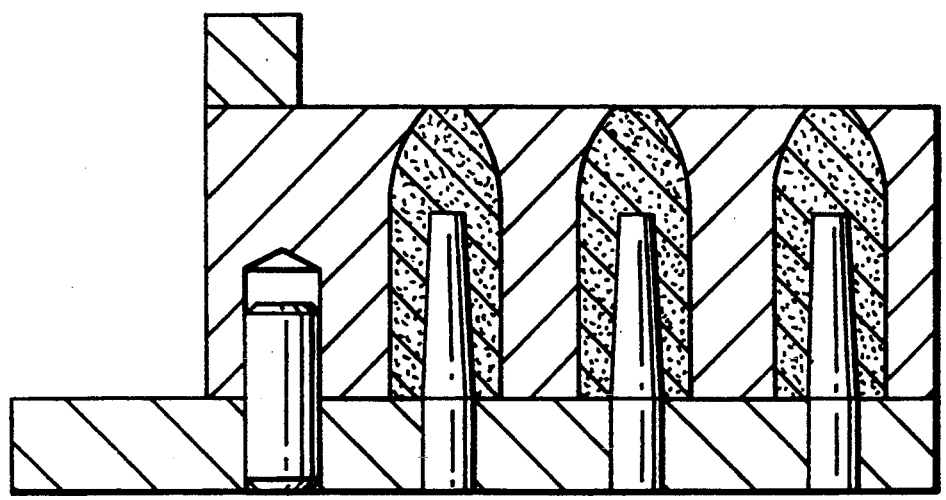

United States Patent [19]
Morton et al.

[11] Patent Number: 5,422,117
[45] Date of Patent: * Jun. 6, 1995

[54] MULTIPHASE PHARMACEUTICAL FORMULATIONS

[75] Inventors: Oswald Morton, London, Great Britain; Koral Embil, Istanbul, Turkey

[73] Assignee: EDKO Trading and Representation Company Ltd., Istanbul, Turkey

[ * ] Notice: The portion of the term of this patent subsequent to May 9, 2012 has been disclaimed.

[21] Appl. No.: 965,403

[22] PCT Filed: Jun. 26, 1991

[86] PCT No.: PCT/EP91/01204

§ 371 Date: Dec. 18, 1992

§ 102(e) Date: Dec. 18, 1992

[30] Foreign Application Priority Data

Jun. 28, 1990 [GB] United Kingdom ............... 9014391
Feb. 19, 1991 [GB] United Kingdom ............... 9103444

[51] Int. Cl.$^6$ ............................. A61F 9/02; A61K 9/14
[52] U.S. Cl. ............................. 424/436; 424/489; 424/DIG. 15; 514/966
[58] Field of Search ............... 424/436, DIG. 15, 489; 514/966; 264/4.1; 428/402

[56] References Cited

U.S. PATENT DOCUMENTS

| | | | |
|---|---|---|---|
| 2,727,846 | 12/1955 | Talbot | 167/63 |
| 3,085,934 | 4/1963 | Vierling | 167/53 |
| 3,098,795 | 7/1963 | Kreps | 167/90 |
| 3,415,249 | 12/1968 | Sperti | 128/271 |
| 3,881,012 | 4/1975 | Minma et al. | 424/436 |
| 3,917,825 | 11/1975 | Matsuzawa et al. | 424/177 |
| 4,198,390 | 4/1980 | Rider | 424/21 |
| 4,690,823 | 9/1987 | Lohner et al. | 424/456 |
| 4,690,825 | 9/1987 | Won | 424/501 |
| 4,812,480 | 3/1989 | Shirakura et al. | 514/557 |
| 4,873,091 | 10/1989 | Jankower et al. | 424/489 |

FOREIGN PATENT DOCUMENTS

| | | | |
|---|---|---|---|
| 828140 | 11/1969 | Canada | 167/125 |
| 0211298 | 2/1987 | European Pat. Off. | A61K 7/035 |
| 0306236 | 3/1989 | European Pat. Off. | |
| 914925 | 1/1963 | United Kingdom | |
| 8801164 | 2/1988 | WIPO | |
| 8910132 | 11/1989 | WIPO | |
| 9007324 | 7/1990 | WIPO | A61K 9/02 |
| 9007326 | 7/1990 | WIPO | |

OTHER PUBLICATIONS

Hara, Kenji, "Anti-inflammatory topical formulations containing silicone oil and other oils with low melting point," *Chemical Abstracts*, vol. 105, 1986, p. 396.
*Remington's Pharmaceutical Sciences*, 15th Ed., pp. 713–714, Mack Publishing, Easton, Pa. (1975).
*Remington's Pharmaceutical Sciences*, 15th Ed., pp. 1546–1553, Mack Publishing, Easton, Pa. (1975).
Reynolds, James E., Editor, *Martindale The Extra Pharmacopoeia*, pp. 1325–1326, The Pharmaceutical Press, London (1989).
*Pharmaceutical Dosage Forms*, vol. 3, p. 119, 162–164, Marcel Dekker, Inc., New York & Basel (1984).

*Primary Examiner*—Thurman K. Page
*Assistant Examiner*—Carlos Azpuru
*Attorney, Agent, or Firm*—Rothwell, Figg, Ernst & Kurz

[57] ABSTRACT

The invention provides a multiphase pharmaceutical composition for combatting skin and anorectal conditions requiring medication comprising at least one phase containing one or more medicaments for combatting said disease and at least one porous phase containing a silicone oil absorbed therein and adapted for release, preferably delayed release, of the silicone oil whereby application of said composition at a region affected by said skin or anorectal condition deposits said medicament or medicaments thereon and a layer of silicone oil is formed thereover thus protecting the medicaments from erosion by aqueous media.

13 Claims, 1 Drawing Sheet

MULTIPHASE PHARMACEUTICAL FORMULATIONS

This invention concerns pharmaceutical formulation for the treatment of skin and anorectal conditions.

Skin diseases commonly require the frequent application of medicaments. It is commonly preferably to leave the site of application uncovered although there is then a tendency for the medicament to be removed by contact with moisture. This is particularly true in the cases of anorectal diseases such as haemorrhoids and anal fissures which are commonly treated with combinations of astringents, antiseptics, topical analgesics, vasoconstrictors, antispasmodics and antiinflammatory steroids. However, the healing of the lesions is commonly inhibited by the mucous environment which, for example, leads to maceration of moist perianal skin.

One possible solution to this problem would be to apply medicaments in an occlusive layer which would repel water from the treated area. However, such conditions tend also to cause retention of fluids produced by the tissues, so that such an occlusive layer, by producing maceration of the affected area would thereby exacerbate the problem.

Furthermore, it is difficult to ensure that the occlusive layer does not form a barrier to prevent the medicaments from reaching the intended site of application.

On the other hand, at internal sites a deposited occlusive layer, for example of suppository base containing medicaments, is subject to erosion by aqueous media which can quickly reduce the beneficial effect of the medicament(s).

Our copending International Patent Application No. PCT/GB89/01545 describes and claims a multiphase pharmaceutical composition for combatting an anorectal disease comprising at least one phase containing one or more medicaments for combatting said disease and at least one phase adapted for delayed release of a silicone oil whereby application of said composition at a region affected by said disease deposits said medicament or medicaments thereon and a layer of silicone oil is formed thereover, so protecting the medicaments from erosion by aqueous media.

In our above International application, the means for delayed release of silicone oil include microcapsules containing the silicone oil which release the latter on rupture of the microcapsule shell, for example by pressure, dissolving or melting. The present invention is based on the concept of using, as the means for delayed release of silicone oil, one or more porous phases having silicone oil absorbed therein.

According to the present invention therefore we provide a multiphase pharmaceutical composition for combatting skin and anorectal conditions requiring medication comprising at least one phase containing one or more medicaments for combatting said disease and at least one porous phase containing a silicone oil absorbed therein and adapted for release, preferably delayed release, of the silicone oil whereby application of said composition at a region affected by said skin or anorectal condition deposits said medicament or medicaments thereon and a layer of silicone oil is formed thereover thus protecting the medicaments from erosion by aqueous media.

It will be appreciated that by being released after the application of the medicament, the silicone oil does not form a barrier between the medicament and the skin but forms a layer over the medicament which protects it from erosion while allowing the passage of water vapour and thus avoiding some of the problems of occlusive layers.

Skin conditions which may usefully be treated by compositions according to the invention include eczema, dermatitis, dry skin, chapped skin, napkin rash, pruritis and mild burns such as sunburn.

The porous phase(s) may be adapted to release the silicone oil by diffusion, possibly aided by the action of pressure to compress the particles, dissolution or melting.

In general, the porous phase(s) comprise porous particles.

A wide range of porous particles are available, as described in International Patent Applications WO88/01164 and WO89/10132, U.S. Pat. Nos. 4,873,091 and 4,690,825 and European Patent Application 306236A, the contents of which are incorporated herein by reference.

In such porous particles, the total pore volume is preferably in the range 0.1 to 2.0 ml/g, more preferably 0.3 to 1.0 ml/g. The diameters of the particles will generally be in the range 1 to 1000 microns, preferably 5 to 100 microns, more preferably 10 to 50 microns: the surface area of the particles will generally range from about 1 to 500 $m^2/g$, preferably 20 to 200 $m^2/g$.

The porous particles may be composed of a wide range of materials. Many organic, synthetic polymers are suitable, as well as natural substances such as cellulose or gelatin. The choice of material will depend in part on the intended means of delayed release of the silicone oil, i.e. diffusion, compression, dissolving or melting.

Where diffusion of the silicone oil is intended, the porous particles may be relatively rigid. This has the advantage that the outermost pores do not collapse when the oil diffuses out and thus do not block the diffusion of the oil from the inner pores. Such rigidity can be controlled by the degree of cross-linking of polymeric materials of which the particles are composed. The degree of cross-linking will generally be at least 10%, more usually in the range 20 to 80%, for example 25 to 60%.

Polymers of which the particles may be formed include polyolefins, including polyethylene, polystyrene, polydicyclopentadiene etc.; polyacrylate esters, e.g. optionally alkoxylated $C_{1-10}$ alkyl, cycloalkyl, aryl or aralkyl esters of polyacrylic or polymethacrylic acids; polyvinyl esters e.g. polyvinyl acetate or polyvinyl laurate; polyvinyl ketones, e.g. polyvinylmethyl ketone; and polyvinyl ethers, e.g. polyvinylpropyl ether.

The silicone oil will preferably be a polydialkylsiloxane oil, more preferably polydimethylsiloxane. Suitable medical grade silicone oils include Dow Corning 360 Medical Fluid.

In one embodiment of the invention the composition comprises a cream containing the medicament(s) together with porous particles containing silicone oil which release said oil after application of the composition to the affected area.

As indicated above, the porous particles in such a cream may liberate the silicone oil by diffusion, pressure, dissolving or melting. It is preferred that the particles are elastically compressable so that after first application of the cream whereby the medicament contacts the infected area, application of gentle pressure, for example by rubbing, causes rapid release of the silicone oil to provide a coating of oil over the layer of cream.

Elastically compressable particles may be composed of elastomers, such as those described in U.S. Pat. No. 4,873,091, including for example, isoprene rubbers, butadiene rubbers, chloroprene rubbers, styrene butadiene. Particularly useful are ethylene-propylene-diene terpolymers, wherein the diene components may be straight chain diolefins, cyclic dienes and bicyclic dienes. Examples of such dienes include 1,4-hexadiene, dicyclopentadiene and ethylidene norbornene. Silicone rubbers may also be used.

Porous particles which dissolve, primarily in aqueous body fluids, may be composed of water-soluble gels including gelatin, agarose etc and certain polymethyl methacrylates such as Eudragit (Röhm, Darmstadt) which dissolve at the pH of the rectum.

Porous particles which melt may be composed of fats and waxes of the type used in suppositories which melt at body temperatures but which are solid at room temperature as well as gelatin.

The phase in which the medicament(s) are contained may be a conventional cream base, e.g. containing oily or waxy materials such as liquid paraffin, white petroleum or cetyl alcohol, water and one or more surfactants to produce a water-in-oil emulsion. A bactericide such as benzalkonium chloride is conveniently present.

Medicaments which may usefully be present include astringents such as bismuth subgallate, local anaesthetics such as benzocaine or lignocaine, cortico steroid, antiinflammatory steroids such as hydrocortisone acetate, antibacterials and emollients.

According to a further embodiment of the invention, compositions for the treatment of anorectal diseases take the form of a suppository comprising an outer layer containing the medicament in a suppository base surrounding one or more porous phases containing the silicone oil.

The suppositories may be provided with a gauze attachment as described in our International Patent Application No. PCT/GB89/01547 to assist location in the anorectal area.

The medicaments and silicone oil may be as described above for the creams according to the invention.

The suppository base may, for example, be any conventional suppository base material such as glycogelatin, polyethylene glycol, fractionated palm kernel oil or, more preferably, one or more natural, synthetic or semi-synthetic hard fats such as cocoa butter. A particularly preferred material is one of the range of cocoa butter products sold under the trade name Witepsol by Dynamit Nobel, Slough, England.

The porous phase(s) may conveniently be porous particles which may be dispersed throughout the suppository base or, more preferably, are concentrated in the interior of the suppository.

The porous phase may also be a single, relatively large porous body. If this is readily compressible, i.e. of a spongy consistency, it will release a substantial volume of the silicone oil by pressure from the walls of the rectum. If this porous body is located in the centre of the suppository, release of the silicone oil will be delayed until the suppository base has melted, thus allowing the medicament to contact the affected area before being coated by the silicone oil.

However, the porous body containing the silicone oil may comprise one side of an asymmetrical suppository in which the other side is the supository base carrying the medicament. Such an asymmetrical suppository may be of use where the affected area is localised on one side of the anus and can then be inserted in such a way that the suppository base with medicament contacts the affected are a while the silicone oil-containing porous body overlies this and releases silicone oil by pressure of the walls of the anus. In this case, the silicone oil may begin to be released immediately on application, i.e. release will not be delayed until after melting of the suppository base. However, the porous body with absorbent silicone oil will overlie and thus protect suppository base in the immediate vicinity of application while silicone oil will exude to cover more widespread melted suppository base.

Suppositories according to the invention can be made in any convenient way,. Thus, for example, the outer suppository layer may be cast in conventional suppository moulds into which one or more pins or rods protrude longitudinally. After solidification, the pins may be removed, the moulds may be inverted and the phase containing the silicone oil introduced into the cavity left by removal of the pins. If the material so introduced does not fill the cavities completely, the remainder of the space can advantageously be filled with further suppository base material to ensure that the silicone oil-containing phase is completely surrounded by suppository base material. Where the porous phase comprises porous particles, these may be simply distributed throughout the melted suppository base and the suppositories may then be cast conventionally.

Porous materials for use in compositions of the invention may be made in any convenient way. Thus, it is possible to polymerise one or more suitable monomers in the presence of a dispersed porogen: after polymerisation, the porogen may be removed, e.g. by evaporation or solvent extraction, to provide a network of interconnected pores. The silicone oil can then be absorbed into the porous material, if desired by first evacuating air from the pores. The silicone oil can, however, itself be used as the porogen: the silicone oil may be dispersed in droplets throughout a monomer with which it is immiscible so that after polymerisation the silicone effectively fills pores within the polymeric material. In general, however, it is preferred to prepare the porous material first in order to remove rigorously all traces of monomer, catalysts and cross-linking agents, before introduction of silicone oil.

A number of possible methods of manufacture of porous material, in particular porous particles, are described in the prior patents listed above.

In general, porous particles may conveniently be produced by emulsion or suspension polymerisation in a liquid - liquid system. Thus, for example, a solution comprising the chosen water-immisicible monomer, any cross-linking agent required, a catalyst, if needed, and a porogen which is misicible with the solution but immisicible with water. The solution is then suspended in an aqueous solution, which may contain one or more suspending agents or surfactants and polymerisation is initiated e.g. by raising the temperature or by irradiation. The porogen is then removed from the solidified particles, e.g. by evaporation or extraction into a solvent which is substantially inert to the polymer.

Examples of such porogens include $C_{5-12}$ alkanes, $C_{5-8}$ cycloalkanes and aromatic solvents such as benzene toluene etc. The particles will normally be washed thoroughly to remove contaminants, using solvents such that the final solvent can be removed by evaporation.

In general, particle diameter may be controlled by the degree of agitation to prepare the initial emulsion. The pore diameter and pore volume are controlled by the amount of porogen used and the degree of cross-linking.

The monomers used to prepare the particles may be any of those appropriate to make the polymers set out above. Suitable cross-linking agents for mono-olefins include poly-ethylenically unsaturated monomers.

The following Examples are given by way of illustration only:

EXAMPLE 1

| Cream | |
|---|---|
| | % |
| Dow Corning 360 Silicone oil (dimethasone) absorbed in polystyrene-divinylbenzene porous beads, mean particle diameter 30 microns, pore volume 0.5 ml/g | 10 |
| Liquid paraffin | 22.75 |
| White petrolatum | 8.0 |
| Cetyl alcohol | 7.0 |
| Span 60 | 3.0 |
| Benzocaine | 2.5 |
| Bismuth subgallate | 2.0 |
| Potassium dihydrogen phosphate | 0.5 |
| 1% Aqueous Benzalkonium chloride | 10.0 |
| Tween 60 | 5.0 |
| 70% Aqueous sorbitol | 5.0 |
| Hydrocortisone acetate | 0.5 |
| Water | 23.75 |

The oily phase comprising the liquid paraffin, white petrolatum, cetyl alcohol and Span 60 are mixed at 60°. The aqueous phase comprising the remaining components except the porous beads is also blended at 60° C. and the two phases combined and blended. The porous beads are added subsequently and dispersed throughout the cream.

EXAMPLE 2

| Suppository | |
|---|---|
| Dow Corning 360 Silicone oil (dimethasone) absorbed in polystyrene-divinylbenzene porous beads, mean particle diameter 30 microns, pore volume 0.5 ml/g | 10% |
| Bismuth subgallate | 2.0 g |
| Benzocaine | 2.5 g |
| 50% Benzalkonium chloride | 0.2 g |
| Hydrocortisone acetate | 0.5 g |
| Witepsol S55 suppository base | 72.15 g |
| Witepsol E85 suppository base | 12.65 g |

The above components apart from the porous particles containing silicone oil are blended at 55° C., cooled to 40° C. and poured into 50 moulds as shown in FIG. 1 hereinafter. After cooling, the pins are withdrawn, the moulds are inverted and porous particles introduced into the cavity left by each pin. The remainder of the cavity is filled with a blend of the two Witepsol bases at 40° C. After chilling, the suppositories are removed from the moulds and packaged.

We claim:

1. A multiphase pharmaceutical composition for combatting skin and anorectal conditions requiring medication comprising at least one phase containing a therapeutically effective amount of one or more medicaments for combatting said disease and at least one porous phase containing a silicone oil absorbed therein and adapted for release of the silicone oil whereby application of said composition at a region affected by said skin or anorectal condition deposits said medicament or medicaments thereon and a layer of silicone oil is formed thereover thus protecting the medicaments from erosion by aqueous media.

2. A composition as claimed in claim 1, wherein said porous phase is adapted for delayed release of the silicone oil.

3. A composition as claimed in either of claims 1 or 2, comprising a cream containing the medicament(s) together with porous particles containing silicone oil which release said oil after application of the composition to the affected area.

4. A composition as claimed in claim 3, wherein said particles are elastically compressible.

5. A composition as claimed in claim 1 or 2 in the form of a suppository comprising an outer layer containing the medicament in a suppository base surrounding one or more porous phases containing the silicone oil.

6. A composition as claimed in claim 5, wherein said porous phase comprises porous particles which are concentrated in the interior of said suppository.

7. A composition as claimed in claim 1 or 2 in the form of a suppository, wherein the porous phase and the medicaments are positioned asymmetrically.

8. A composition as claimed in claim 3 in the form of a suppository comprising an outer layer containing the medicament in a suppository base surrounding one or more porous phases containing the silicone oil.

9. A composition as claimed in claim 4 in the form of a suppository comprising an outer layer containing the medicament in a suppository base surrounding one or more porous phases containing the silicone oil.

10. A composition as claimed in claim 8 wherein said porous phase comprises porous particles which are concentrated in the interior of said suppository.

11. A composition as claimed in claim 9 wherein said porous phase comprises porous particles which are concentrated in the interior of said suppository.

12. A composition as claimed in claim 3 in the form of a suppository, wherein the porous phase and the medicaments are positioned asymmetrically.

13. A composition as claimed in claim 4 in the form of a suppository, wherein the porous phase and the medicaments are positioned asymmetrically.

* * * * *